US007617929B2

(12) United States Patent
Lee et al.

(10) Patent No.: US 7,617,929 B2
(45) Date of Patent: Nov. 17, 2009

(54) METHOD AND STRUCTURE FOR MIXING DIFFERENT MATERIALS IN A POUCH CONTAINER

(76) Inventors: Jeong-Min Lee, 10-92 Sibun APT. 50, Yeuido-Dong, Youngdungpo-Gu, Seoul (KR) 150-894; Seong-Jae Lee, A-1208, Misung APT. 37, Yeuido-Dong, Youngdungpo-Gu, Seoul (KR) 150-887

( * ) Notice: Subject to any disclaimer, the term of this patent is extended or adjusted under 35 U.S.C. 154(b) by 357 days.

(21) Appl. No.: 10/584,107

(22) PCT Filed: Nov. 9, 2004

(86) PCT No.: PCT/KR2004/002890

§ 371 (c)(1),
(2), (4) Date: Jun. 22, 2006

(87) PCT Pub. No.: WO2005/044430

PCT Pub. Date: May 19, 2005

(65) Prior Publication Data

US 2007/0012580 A1 Jan. 18, 2007

(51) Int. Cl.
*B65D 25/08* (2006.01)
*B67D 5/00* (2006.01)
*A61B 19/00* (2006.01)

(52) U.S. Cl. ...................... 206/222; 222/83.5; 604/416

(58) Field of Classification Search ......... 206/219–222; 604/408–416; 222/83.5, 129; 383/80, 906
See application file for complete search history.

(56) References Cited

U.S. PATENT DOCUMENTS

| | | | | | |
|---|---|---|---|---|---|
| 2,687,130 | A * | 8/1954 | Cohen | ........................ | 206/222 |
| 2,721,552 | A * | 10/1955 | Nosik | ........................ | 206/222 |
| 4,548,606 | A * | 10/1985 | Larkin | ........................ | 206/222 |
| 5,257,986 | A * | 11/1993 | Herbert et al. | .............. | 604/416 |
| 6,305,576 | B1 * | 10/2001 | Leoncavallo | ................ | 206/222 |
| 6,840,373 | B2 * | 1/2005 | Gibler et al. | ................ | 206/219 |

FOREIGN PATENT DOCUMENTS

| | | | |
|---|---|---|---|
| EP | 0 561 322 A1 | | 3/1993 |
| EP | 1 122 186 A1 | | 12/2000 |
| JP | 07-300165 | | 11/1995 |
| JP | 2002-211622 | | 7/2002 |
| JP | 2003-34367 | | 2/2003 |
| KR | 10 2003 0085901 | | 7/2003 |
| WO | WO 01/30665 A1 | | 5/2001 |

* cited by examiner

*Primary Examiner*—Bryon P Gehman
(74) *Attorney, Agent, or Firm*—Westman, Champlin & Kelly, P.A.

(57) ABSTRACT

A structure for mixing different materials in a pouch container includes a spout main body provided with a spout hole through which mixture of first and second materials is exhausted. A cap is removably coupled on an outer portion of the spout hole. The first material is stored therein. A seal member is coupled to a lower end of the tube portion.

11 Claims, 15 Drawing Sheets

【FIG 1】
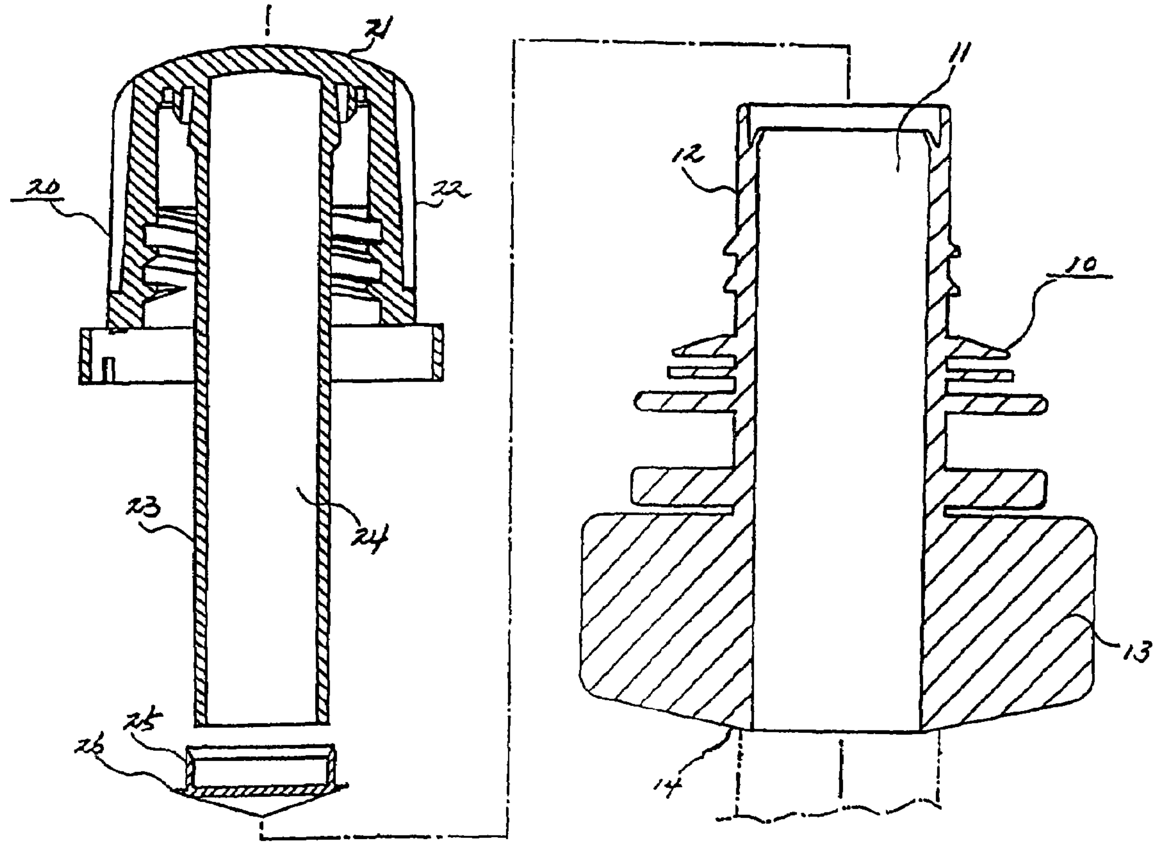
【FIG 2】
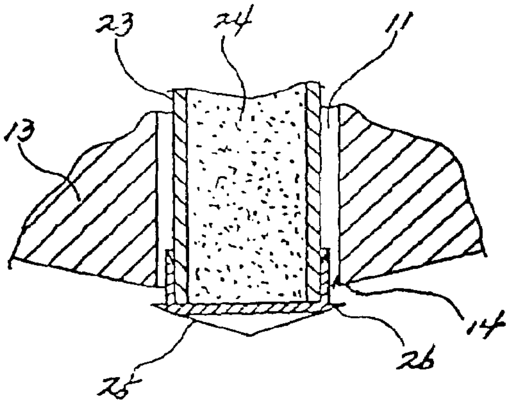

【FIG 3】
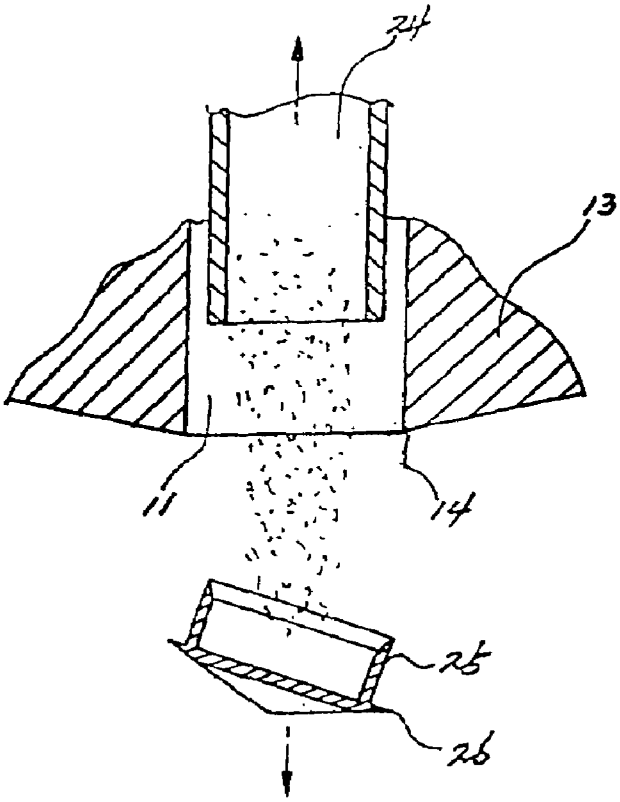
【FIG 4】
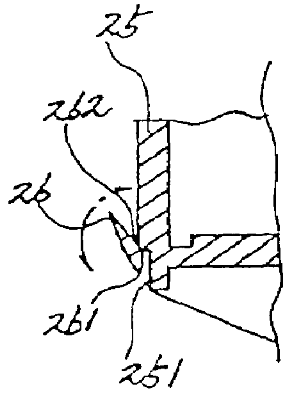
【FIG 5】
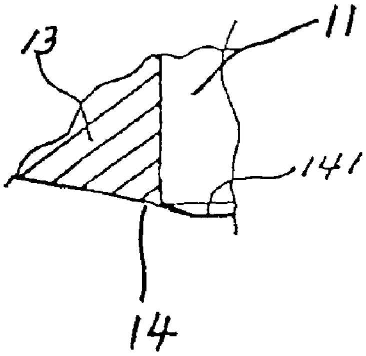

【FIG 6】
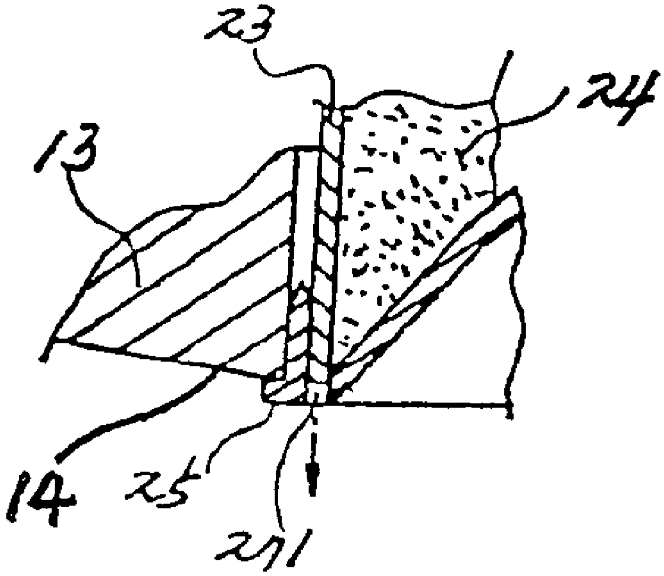
【FIG 7】
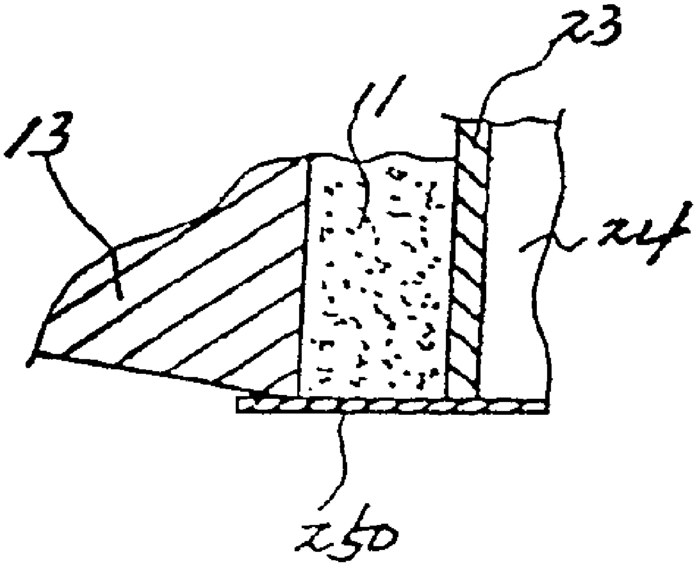

【FIG 8】
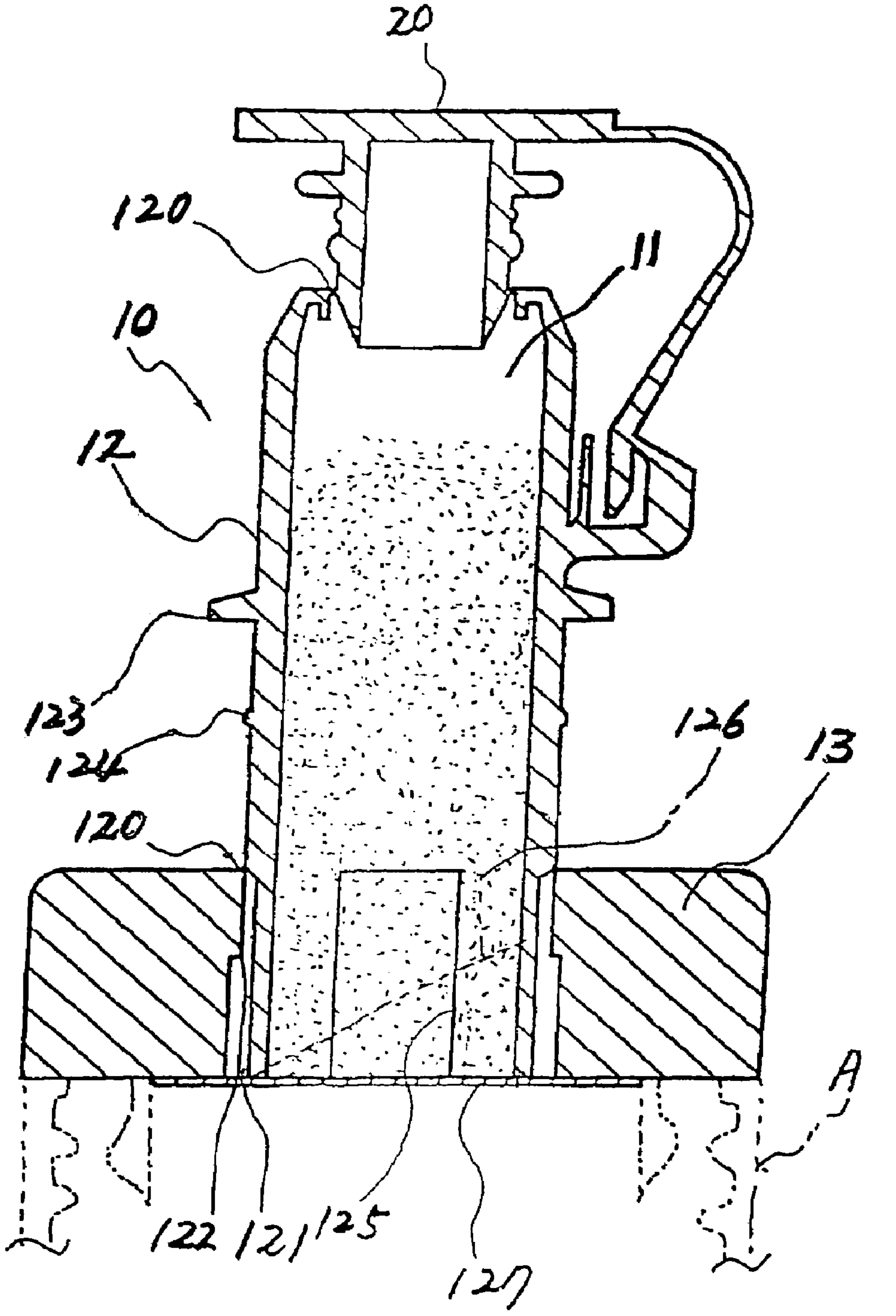

【FIG 9】
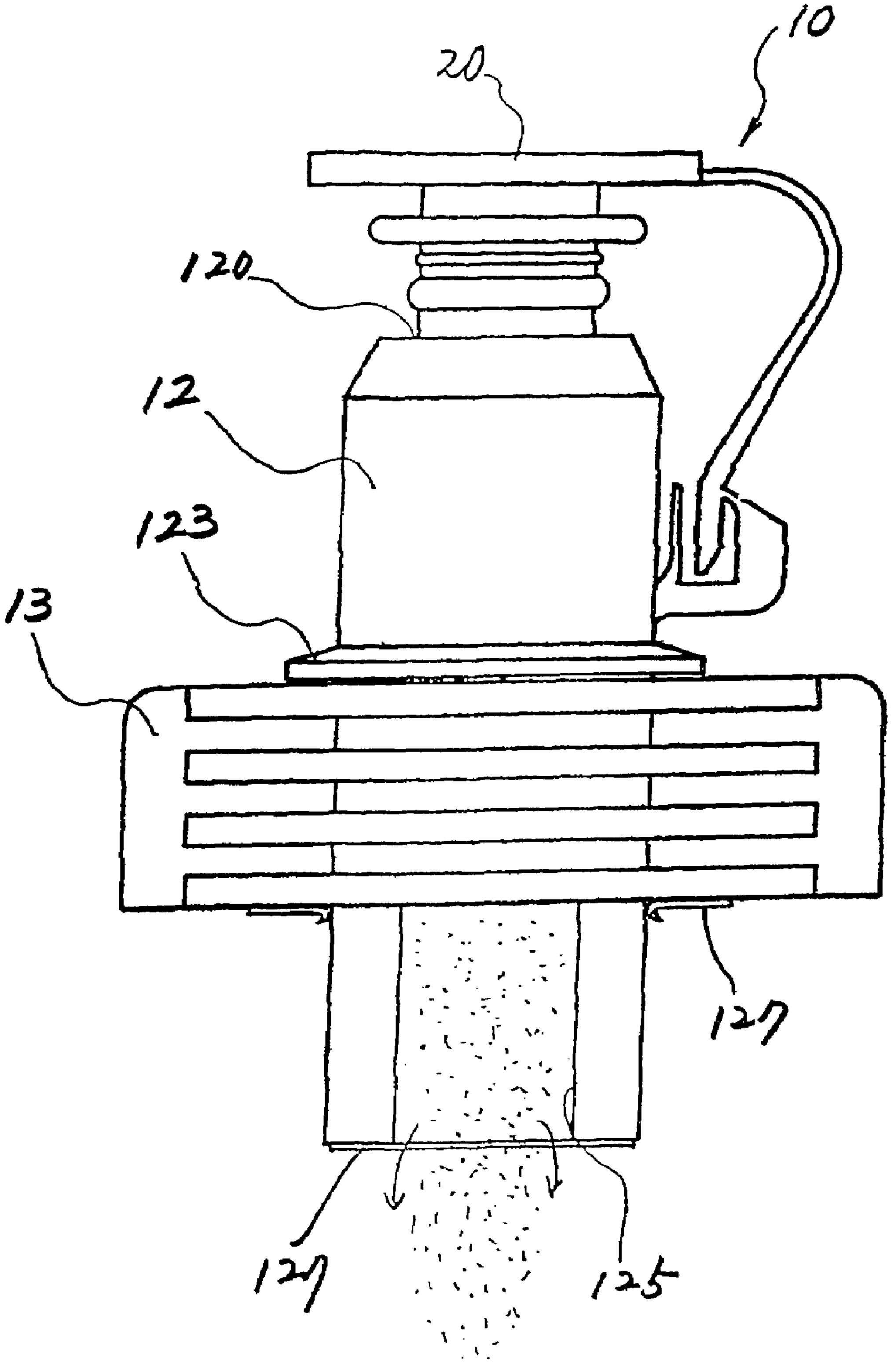

【FIG 10】
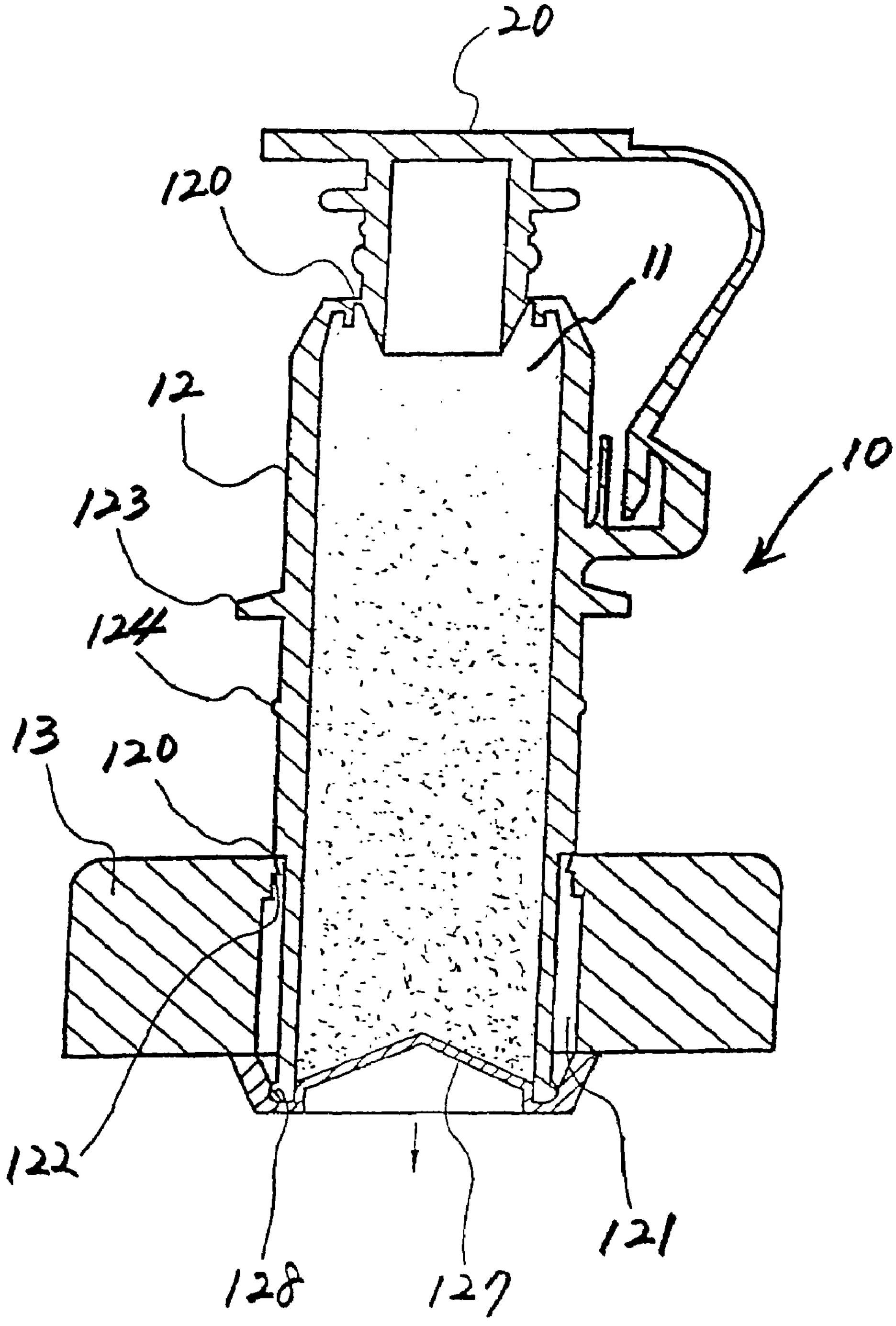

【FIG 11】
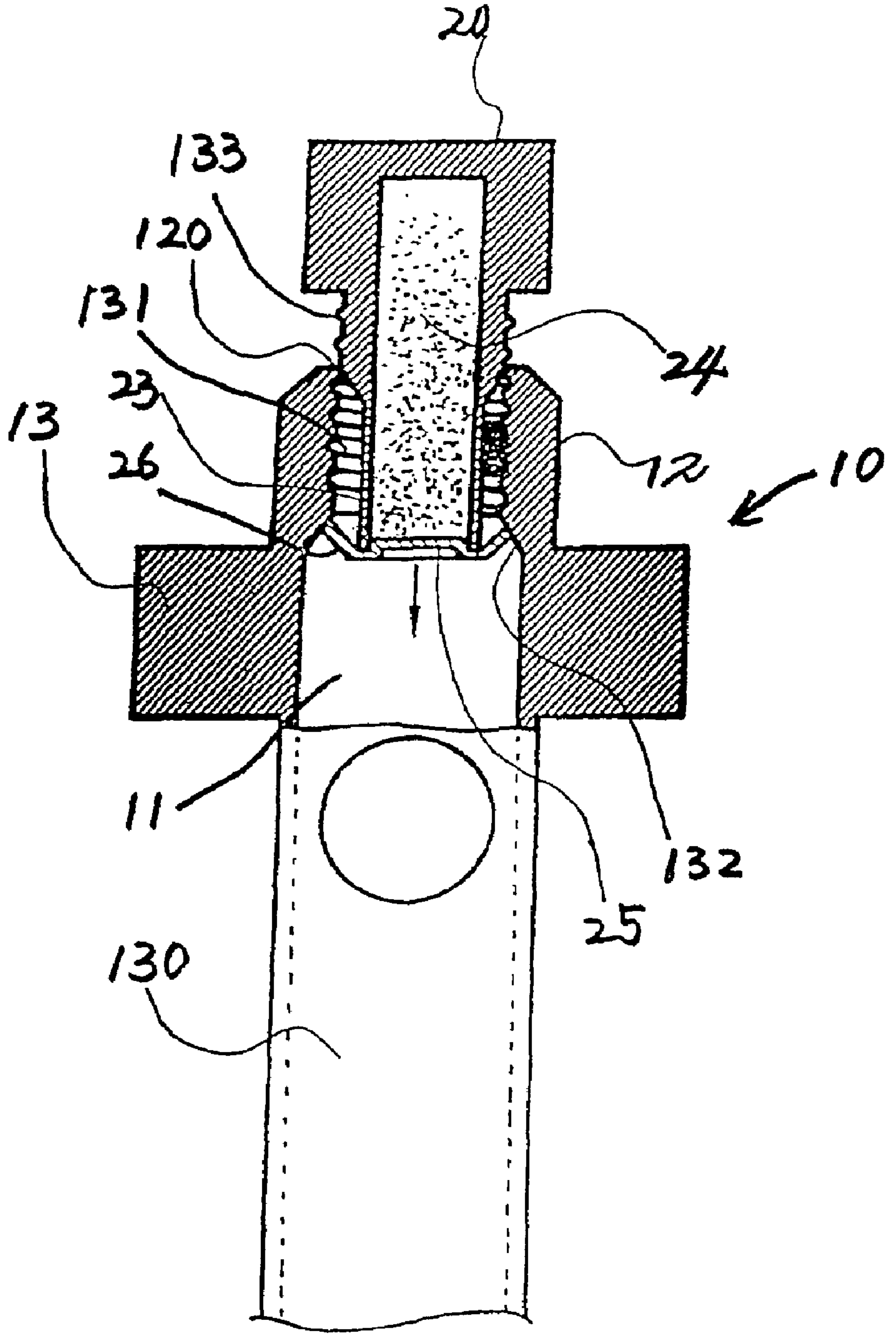

【FIG 12】
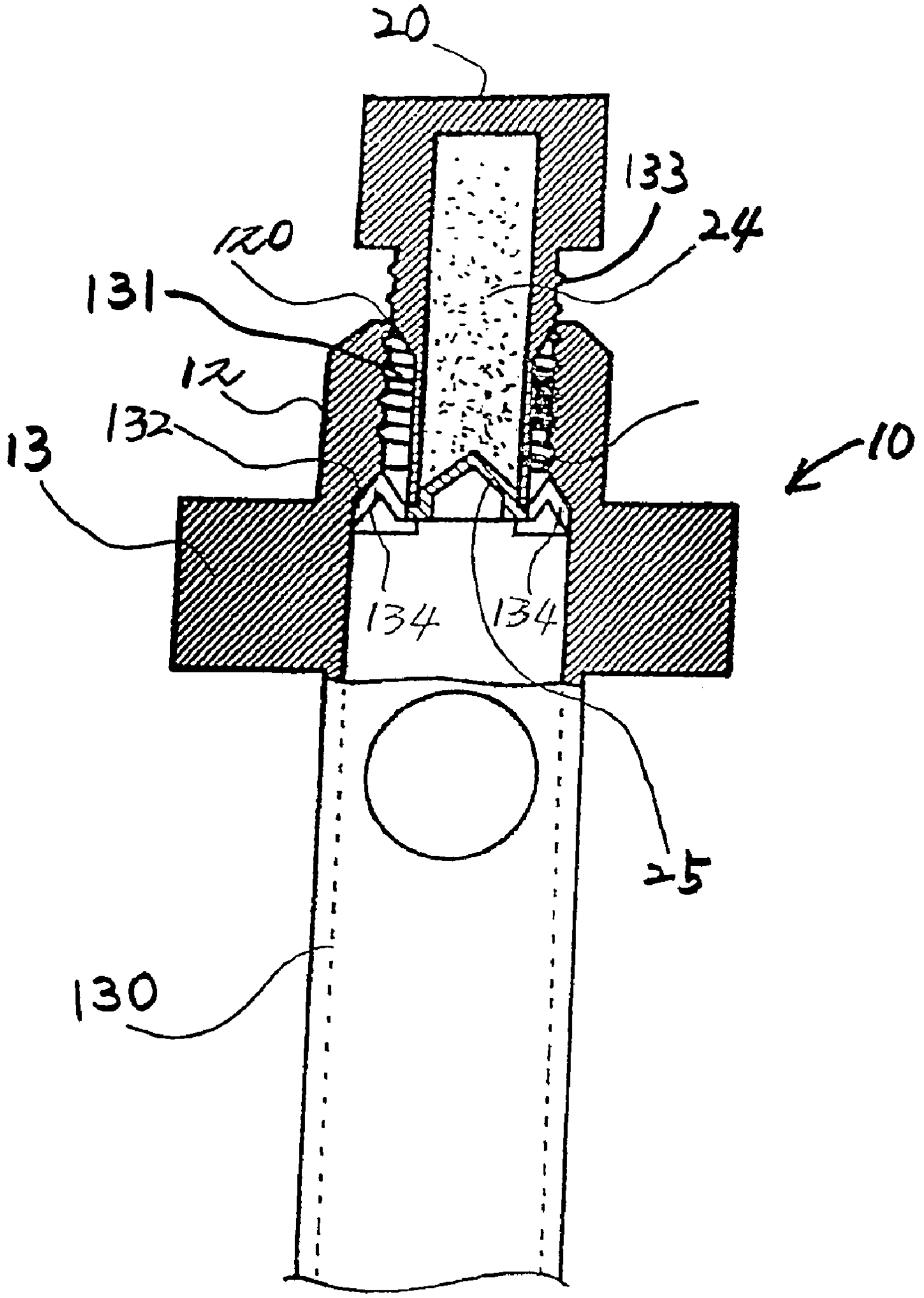

【FIG 13】
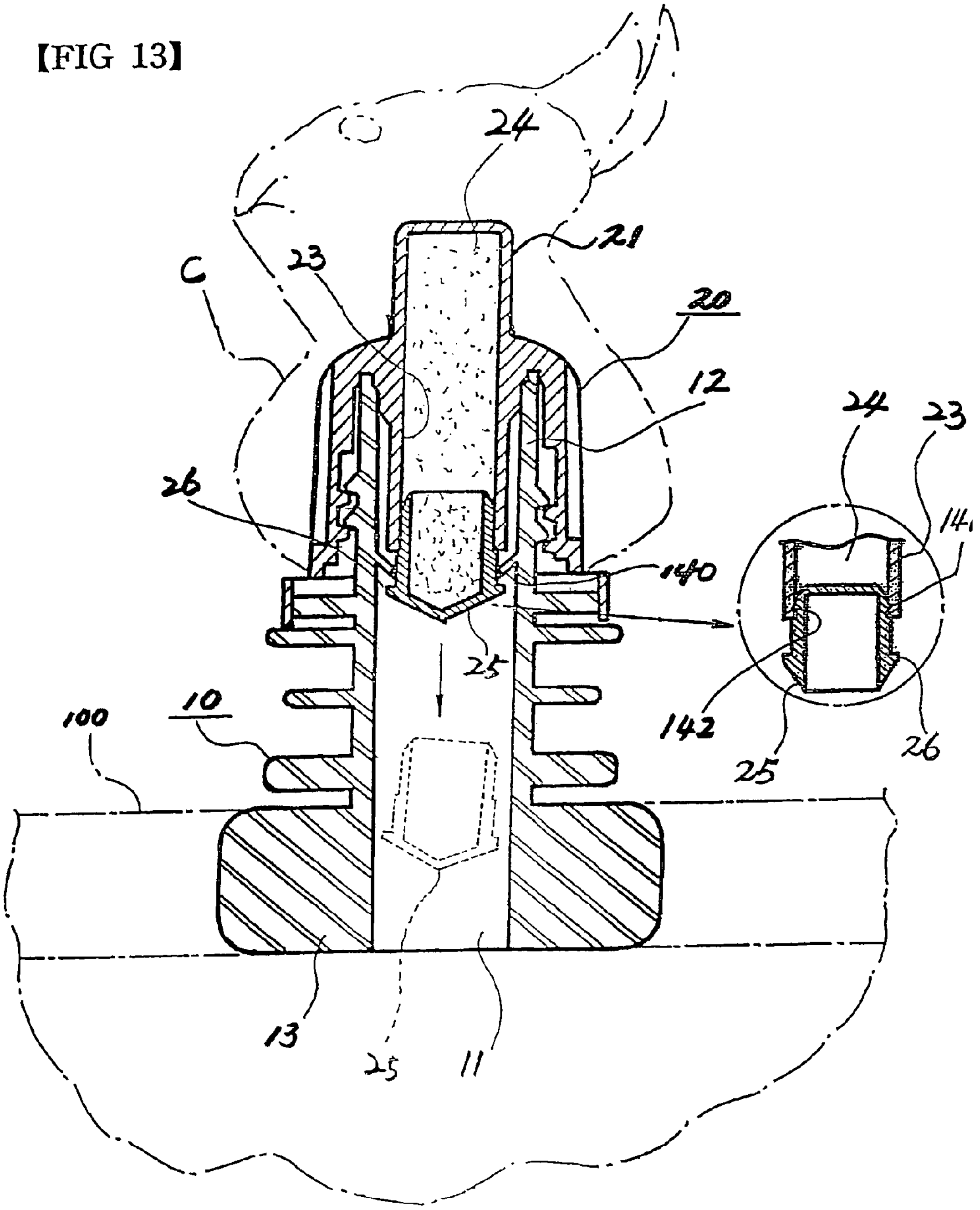

【FIG 14】
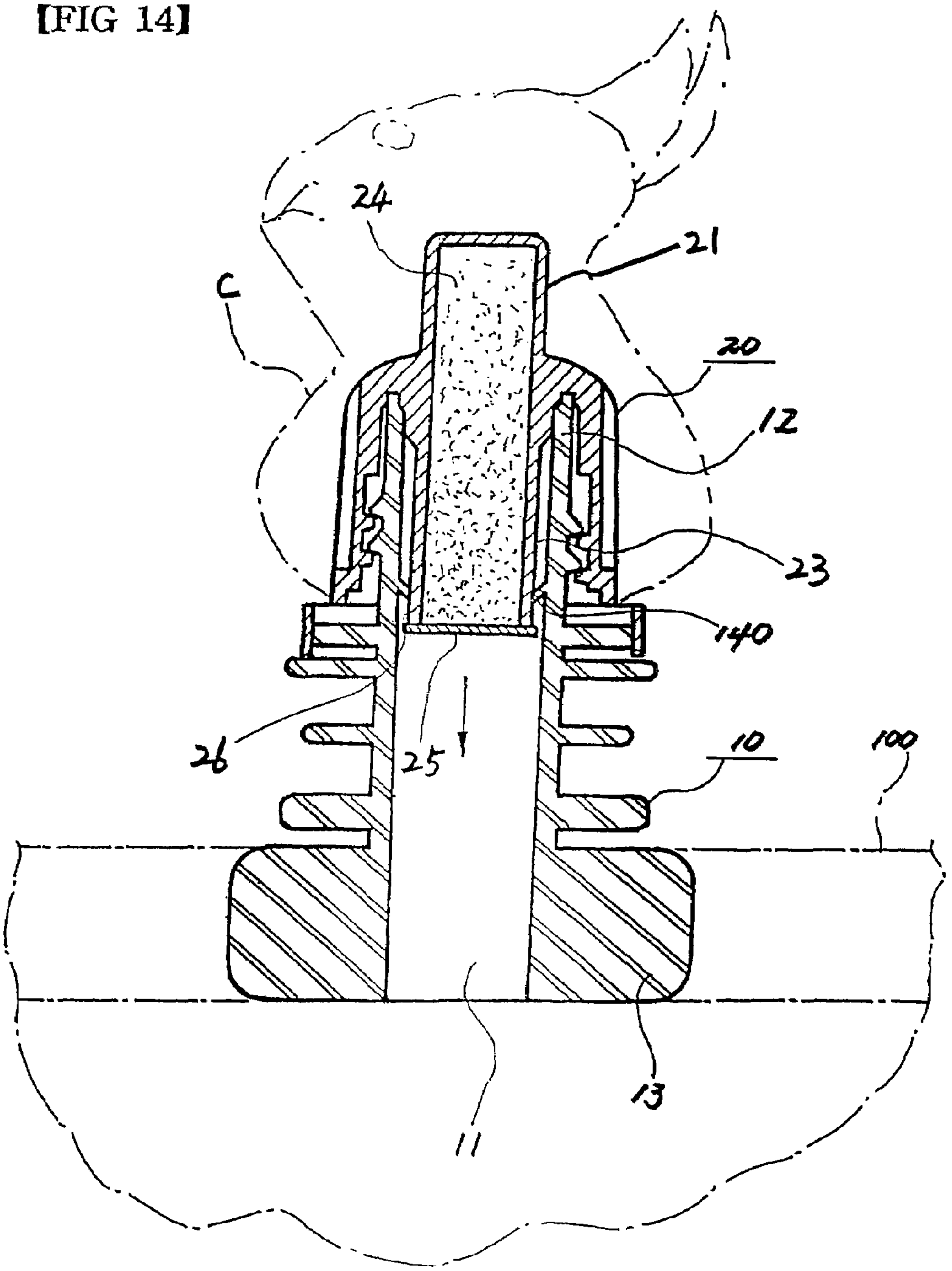

【FIG 15】
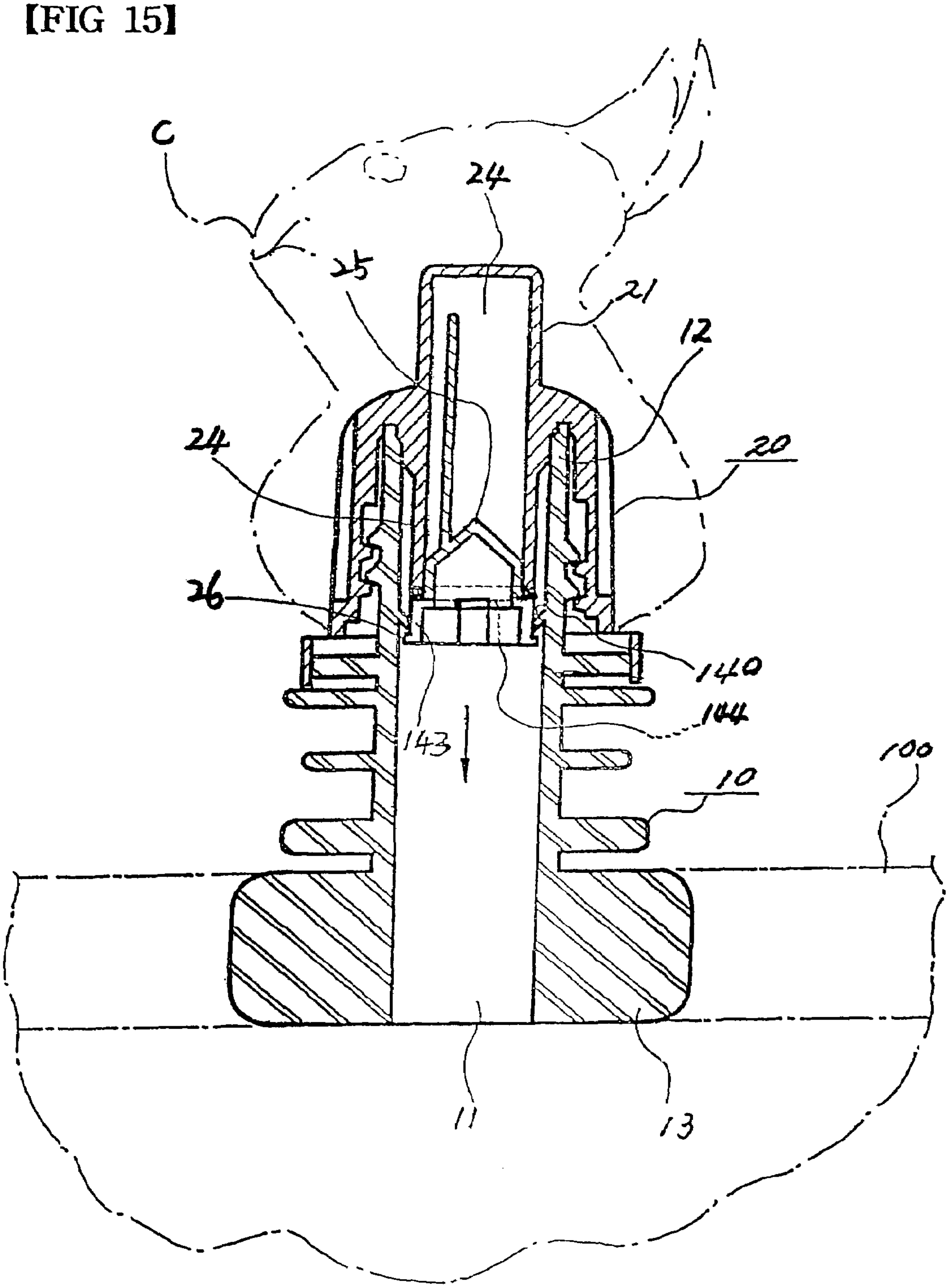

【FIG 16】
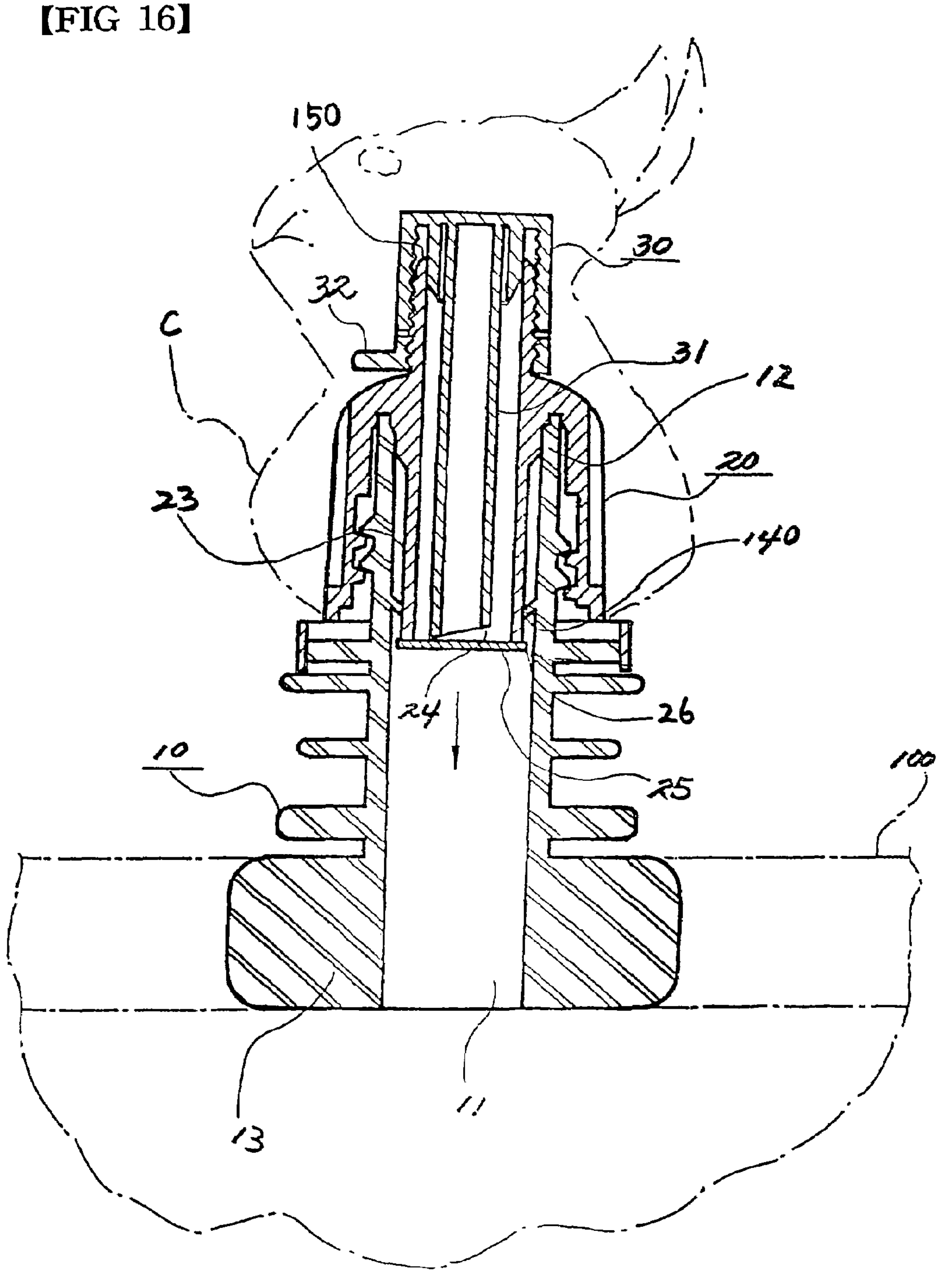

【FIG 17】
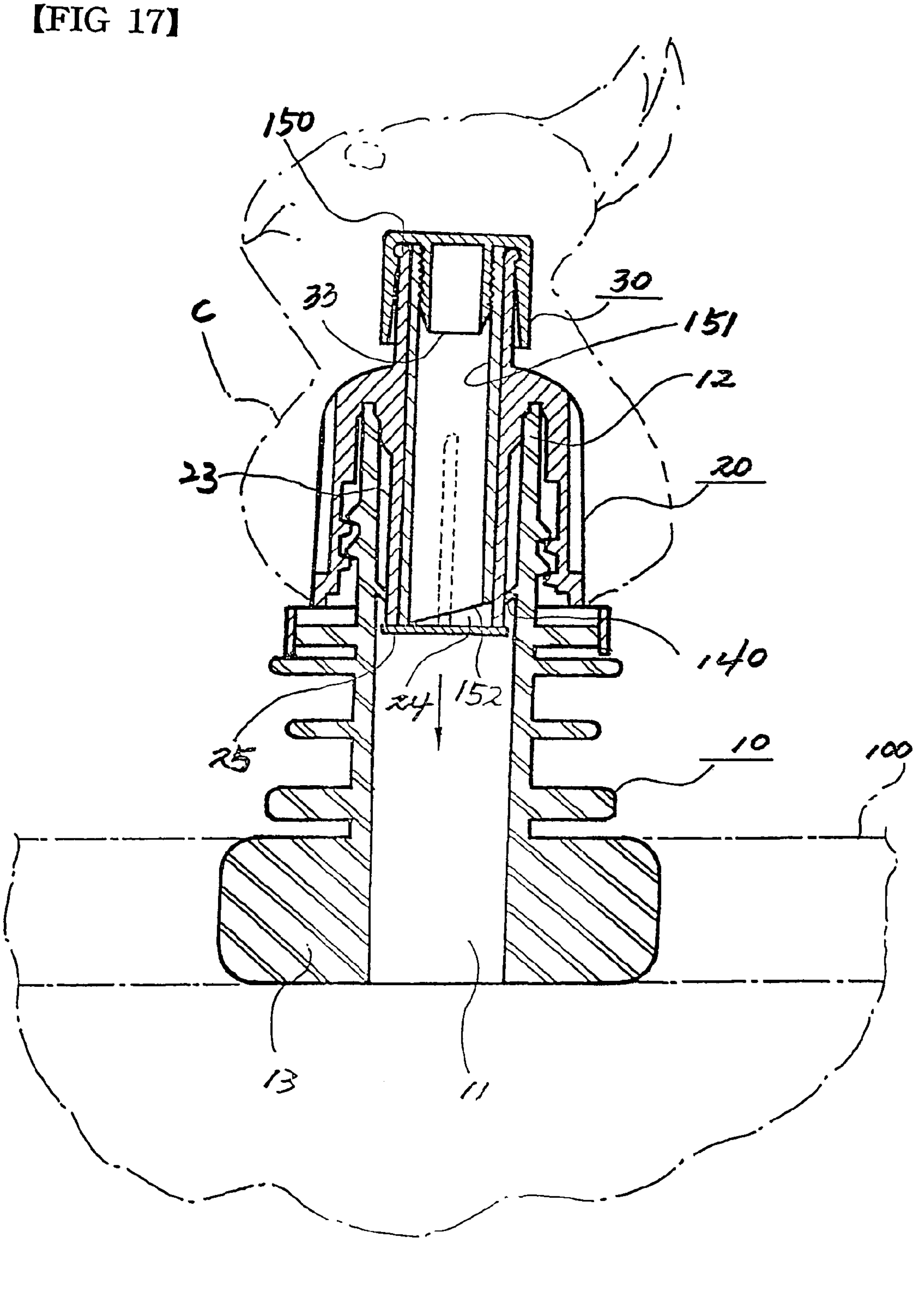

【FIG 18】
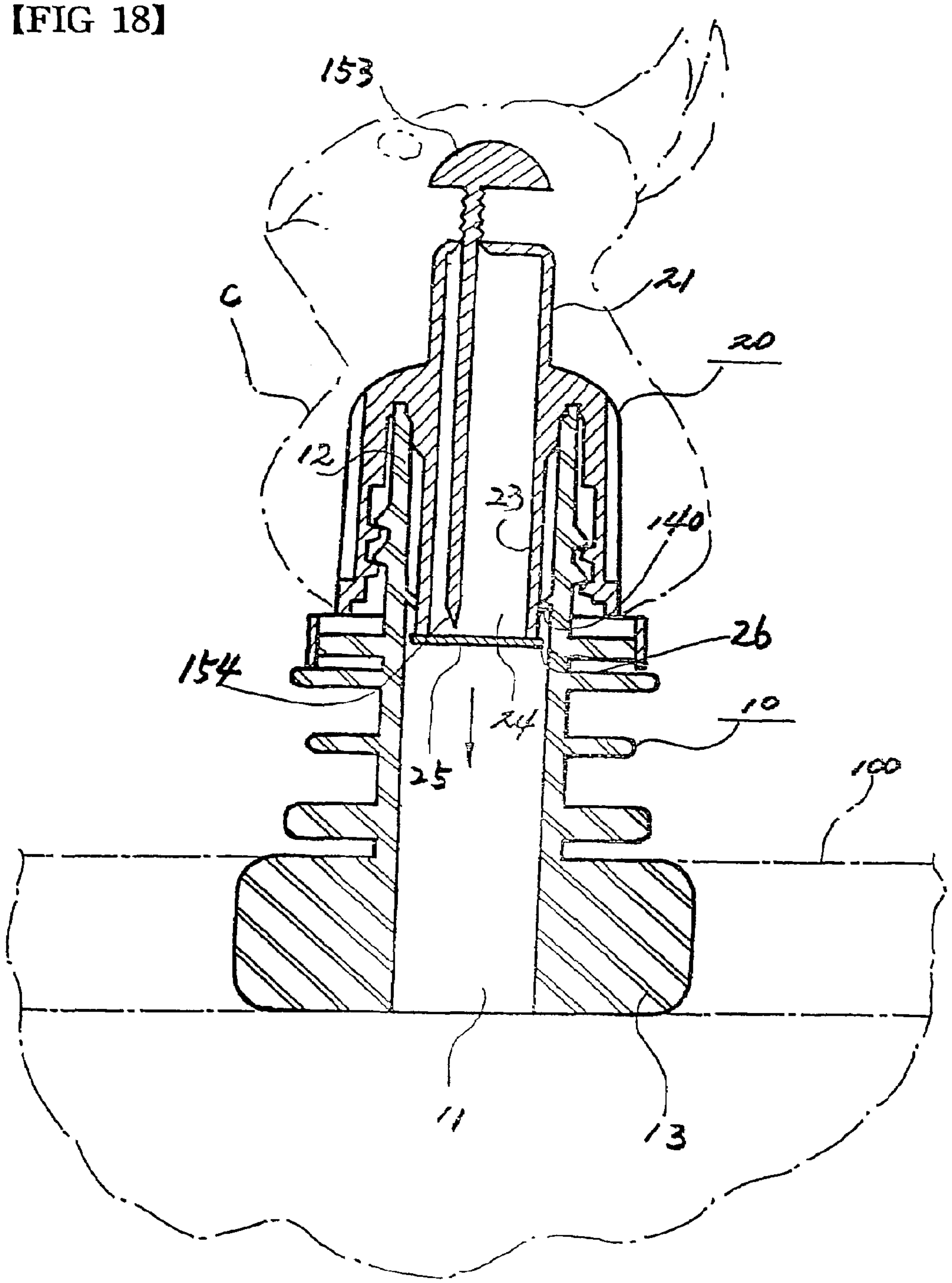

【FIG 19】
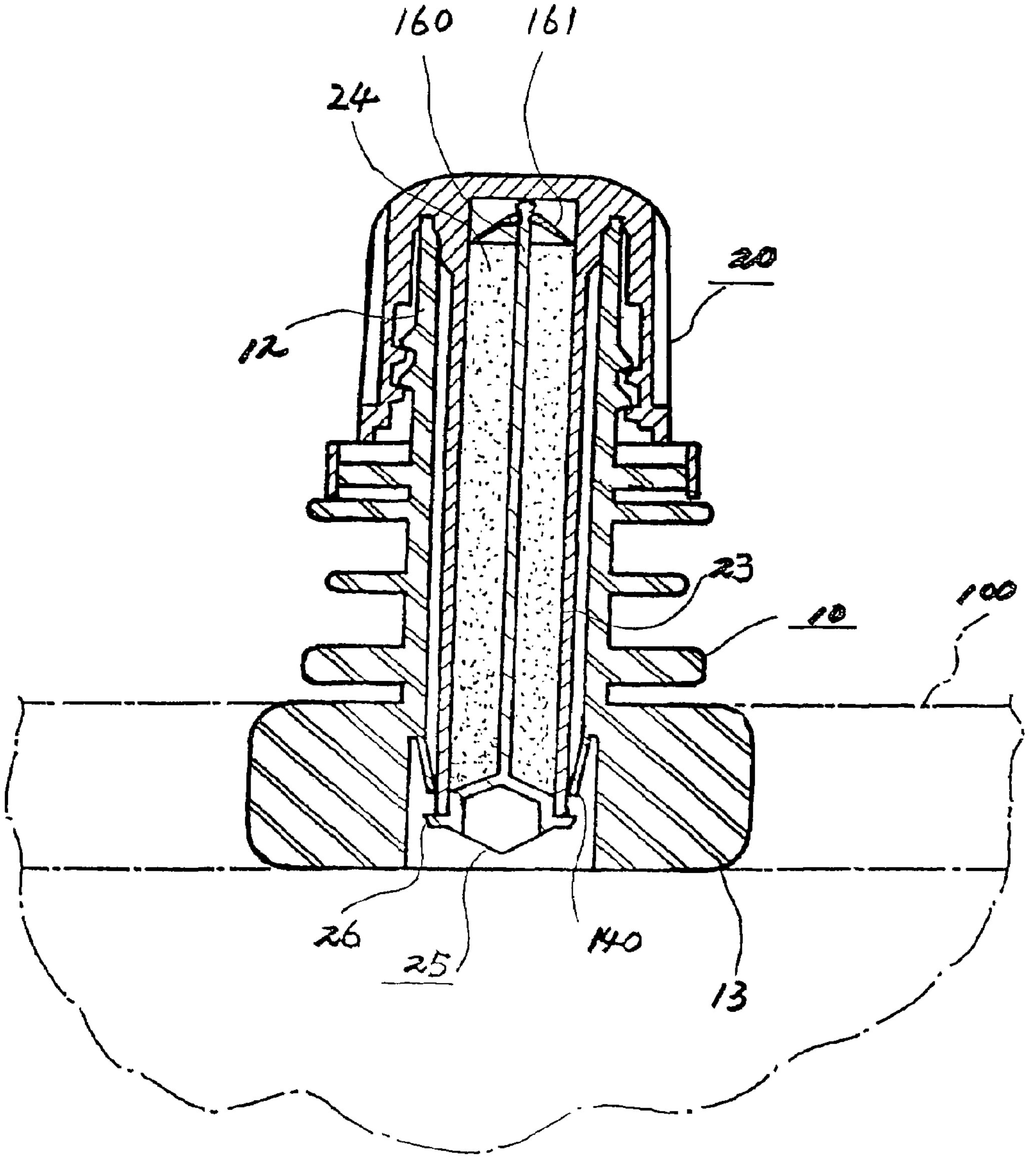

METHOD AND STRUCTURE FOR MIXING DIFFERENT MATERIALS IN A POUCH CONTAINER

CROSS-REFERENCE TO RELATED APPLICATION

This Application is a Section 371 National Stage Application of International Application No. PCT/KR2004/002890, filed Nov. 9, 2004 and published as WO 2005/044430 A2 on May 19, 2005, in English, the content of which is hereby incorporated by reference in its entirety.

TECHNICAL FIELD

The present invention relates to a method and structure for mixing different materials in a pouch container formed of at least one film layer. More particularly, the present invention relates to a method and structure for mixing different materials in a pouch container, in which a space for storing a secondary material is formed on a spout fitted on a spouting portion of the container to effectively mix the secondary material with a primary material contained in the container.

BACKGROUND ART

Generally, a technology for storing a different material in a closure associated with a PET bottle is well known. However, such a technology is not applied to a flexible container as it is difficult to apply the same to spouts having different sizes.

Therefore, a secondary material is filled in the flexible container through the spout. However, it is troublesome to mix secondary material through the spout having a small diameter hole.

In addition, a barrier is installed in the pouch container to store the secondary material. In use, the barrier is removed so that the secondary material can be mixed with a primary material. In this case, it is however difficult to remove the barrier, making it difficult to effectively mix the secondary material with the primary material.

PROBLEM TO BE SOLVED

Therefore, the present invention has made in an effort to solve the above-described problems of the conventional art. It is an objective of the present invention to provide a method and structure for easily mixing different material in a pouch container.

It is another objective of the present invention to provide a method and structure for mixing different materials, which can easily store a first material and mixing the first material with a second material in the pouch container.

It is another objective of the present invention to provide a method and structure for mixing different materials, which can be easily used.

It is another objective of the present invention to provide a method and structure for mixing different materials, which can prevent a first material stored in a storing chamber from being inadvertently leaked.

TECHNICAL SOLUTION

To achieve the above objectives, the present invention provides a method for mixing different materials in a pouch container comprising the steps of storing a first material in a spout assembly fixed on the pouch container; separating a seal member from the spout assembly by operating a cap, thereby releasing the first material into the pouch container by operating a cap; and mixing the first material with a second material in the container.

In another aspect of the present invention, there is provided a structure for mixing different materials in a pouch container, comprising a spout main body provided with a spout hole through which mixture of first and second materials is exhausted; a cap removably coupled on an outer portion of the spout hole and storing the first material therein; and a seal member coupled to a lower end of the tube portion.

ADVANTAGEOUS EFFECT OF THE INVENTION

According to the present invention, a first material such as power and liquid can be stored in a separated chamber and, if required, easily mixed with a second material stored in a container.

In addition, by the simple operation, the first material stored in the separated chamber can be released to be quickly mixed with a second material stored in the container.

Furthermore, since first and second materials are independently stored, it can be prevented that the first material is inadvertently mixed with the second material.

BRIEF DESCRIPTION OF THE DRAWINGS

FIGS. 1 to 7 are views of a first embodiment of the present invention;

FIGS. 8 to 10 are views of a second embodiment of the present invention;

FIGS. 11 and 12 are views of a third embodiment of the present invention;

FIGS. 13 to 15 are views of a fourth embodiment of the present invention;

FIGS. 16 to 18 are views of a fifth embodiment of the present invention; and FIG. 19 is a view of sixth embodiment of the present invention.

BEST MODE FOR CARRYING OUT THE INVENTION

Preferred embodiments of the present invention will be described more in detail hereinafter in conjunction with the accompanying drawings.

FIGS. 1 to 7 show a structure for mixing different materials in a pouch container. As shown in FIG. 1, the inventive structure includes a spout main body 10 attached on a container to exhaust the content out of the container and a cap 20 coupled to the main body 10.

The main body 10 formed in a tube shape defining a spout hole 11. The main body 10 is provided at an upper outer portion with a lip portion 12 to which the cap 20 is coupled and a lower outer portion with a fitting portion fitted on the container. An operation portion 14 is formed under the fitting portion 13.

The cap 20 includes a top portion 21 and a side portion 12 extending from the top portion 21 downward and screw-coupled to the lip portion 12.

A tube portion 23 is formed extending from an inner surface of the top surface 21 and inserted in the spouting hole 11.

The tube portion 23 defines a storing chamber 24 in which a first material that will be mixed with a second material stored in the container by the opening operation of the cap 20 is stored.

As shown in FIG. 2, a seal member 25 is coupled on a lower end of the tube portion 23. The seal member 25 is provided with a peripheral hook step 26 that is hooked on the operating portion 14 when the cap 20 is opened so that the seal member 25 can be separated from the tube portion 23.

Accordingly, by attaching the main body 100 to which the cap 20 is coupled on the container or by coupling the cap 20 to the main body 10 attached on the container, the assembling process is completed.

The first material is filled in the storing chamber 24 defined by the tube portion 23 and the seal member 25 is coupled to the lower end of the tube portion 23. Therefore, the first material is not inadvertently mixed with the second material stored in the container.

In a state where the main body 10 and the cap 20 are assembled, when the cap 20 is screw-opened or moved upward, the tube portion 23 also moves upward. At this point, the hook portion 26 of the seal member 25 is hooked on the operating portion 14 formed on a lower end of the fitting portion 13 so that the seal member 25 can be separated from the tube portion 23.

When the seal member 25 is separated from the tube portion 23, the first material stored in the storing chamber 24 is dropt into the container and mixed with the second material in the container. The user can drink or use the mixed material through the spouting hole 11.

The hook portion 26 is not limited to the above case. For example, as shown in FIG. 4, a supporting step 251 may be formed extending from the bottom of the seal member 25 downward so as to vary the location of the hook portion. The hook portion 26 is provided with a supporting projection 261 that is to be hooked on the supporting step 251 to be limited in its rotation. The hook portion 26 is further provided with a connecting portion that is to be connected to the seal member 25.

Accordingly, when the tube 23 moves upward, the hook portion 25 folded upward is hooked on the operation portion 14 to pivot downward. The supporting projection of the pivoted hook portion 26 is hooked on the supporting step 251 to maintain its outward projected state. At this point, the force applied by the operating portion 14 is transmitted to the hook portion 26, thereby separating the seal member 25 from the tube portion 23 to allow the first material in the storing chamber to be dropt.

Meanwhile, as shown in FIG. 5, when a circumferential projection 141 is formed on a lower-inner portion of the spouting hole 11, it becomes easier to assembly the seal member 15.

As shown in FIG. 6, when a dropping space 271 is formed on a periphery portion of the seal member 25, since the dropping space is opened when the tube portion 23 moves upward, the first material in the storing chamber 24 can be easily dropt.

As shown in FIG. 7, the first material is filled in a space defined between the spouting hole 11 coupled to the cap 20 and the tube portion 23 and the seal member 250 formed of a sheet is attached on the lower end of the tube portion 23. When the cap is screwed, the seal member 250 is broken to allow the first material to be dropt and mixed with the second material in the container.

FIGS. 8 to 10 show a second embodiment of the present invention. The main body 10 of this embodiment is coupled to the fitting portion 13 with a cutting line 120 therebetween. The fitting portion 13 may be integrally formed on the cap A coupled to an opened portion of a pouch container or a neck of a bottleneck.

A space portion 121 is formed between the fitting portion 13 and a lower-outer portion of the main body 10. A hook step 122 is formed on an inner portion of the fitting portion 13.

The spout main body 10 has a lip portion 12 defining a spout hole 11. A circumferential hoop 123 and a circumferential projection 124 are formed around the lip portion 12 and distant from each other by a predetermined distance. A lower end of the main body 10 is provided with an opening 125 through which the first material is released.

The lower end of the lip portion 12 is provided with an inclined lower end 126.

A seal member 127 is attached on the bottom of the fitting portion 13 to independently store the first material in the spout hole 11 of the main body 10. The seal member 126 is attached on only the bottom of the fitting portion 13 or on both the bottom of the fitting portion 13 and the bottom of the spout hole 11.

The cap 20 is integrally formed on the lip portion 12 with a cutting line 128 so that it can be moved away from the lip portion 12 when the user drink the mixed material.

Accordingly, the first material is stored in the spout hole 11 of the main body 10 and the seal member 127 is attached on the fitting portion 13, the first material can be isolated from the second material in the container.

At this point, when the lip portion 12 is pushed downward, the cutting line 120 is broken and the circumferential projection 124 is hooked on the hook step 122 formed on an inner surface of the fitting portion 13, and at the same time, the seal member 127 is broken by the downward movement of the lip portion 12. As a result, the first material is released through the opening 125 to be mixed with the second material in the container.

When the first and second materials are mixed with each other, the cap 20 is separated by cutting the cutting line 120 so that the user can drink the mixed material through the spout hole 11.

In this embodiment, the attachment of the seal member 127 is not limited to the above-structure. For example, as shown in FIG. 10, a hook projection 128 is formed on a lower-outer portion of the lip portion 12 and the seal member 127 can be attached on the lower end of the lip portion 12.

That is, when the lip portion 12 moves upward, since the periphery portion of the seal member 127 is hooked on the bottom of the fitting portion 13. As a result, the seal member 127 is separated from the hook projection 128 and thereby the first material in the spout hole 11 is dropt to be mixed with the second material in the container.

When the lip portion 12 moves downward, the circumferential projection 124 is hooked on the hook step 122, after which the cap 29 is separated from the lip portion 12, the user can drink or use the mixed material through the spout hole 11.

FIGS. 11 and 12 show a third embodiment of the present invention. In this embodiment, the first material is filled inside the cap 20.

The spout main body 10 attached on the opening of the container includes a lip portion 12 and a fitting portion 13 integrally formed on a lower portion of the lip portion 12. A spout guide tube 130 communicating with the spout hole 11 is coupled to a lower portion of the fitting portion 13. The spout hole 11 is provided at an upper-inner portion with a female screw and an inner step 132 formed under the female screw.

The cap 20 coupled on the female screw 131 of the spout hole 11 is integrally formed with the tube portion 12 with a cutting line therebetween. The cap 20 is provided with a tube portion 23 defining a storage space 24 for storing the first material. A lower end of the tube portion 23 is opened. The tube portion 23 is provided at an outer portion with a male screw 133 coupling to the female screw 131.

A seal member 25 is inserted and installed on a lower portion of the tube portion 23. A hook portion 26 is formed on a periphery portion of the seal member 25. The hook portion 26 is designed to be hooked on an inner step 132, thereby separating the seal member 23 from the tube portion 23 to release the first material.

Accordingly, in a state where the first material is stored in the storing space 24 formed inside the tube portion 23, when the seal member 25 is coupled on the lower portion of the tube portion 23, the first material is confined in the storing space 24.

At this point, when the cap 20 moves upward, the hook portion 26 is hooked on the inner step 132, thereby separating the seal member 25 from the tube portion 23 to release the first material out of the storing space 24. The released material is mixed with the second material in the container.

After the above, when the cap 20 is removed from the female screw 131 formed on the inner portion of the lip portion 12, the user can drink or use the mixed material through the spout hole 11.

In this embodiment, as shown in FIG. 12, the seal member 25 is provided at a periphery portion with a dropping space 134. Therefore, when the cap 20 moves upward, and the seal member 25 is separated from the tube portion 23 to allow the first material to be dropt through the dropping space 134.

FIGS. 13 to 15 show a fourth embodiment of the present invention. In this embodiment, a spout main body 10 includes a fitting portion 13 attached on a container 100 and a lip portion 12 having a spout hole. A cap 20 is coupled to the lip portion 12.

A tube portion 23 is formed on an inner top of a top portion 21 of the cap 20. A lower end of the tube portion 23 is opened. The first material is filled in the tube portion 23 and a seal member 25 is removably inserted in the opened lower end of the tube portion 23. A hook portion 26 is formed on a periphery portion of the seal member 25.

The spout hole 11 is provided with a plurality of hook steps 140 on which the hook portion 26 of the seal member 25 is hooked so that the seal member 25 is separated from the tube portion 23. The hook steps 140 are inclined downward and inward.

The seal member 25 is provided at an outer portion with a projection 141 that is to be inserted in a groove 142 formed on an inner portion of the tube portion 23 so as to prevent the seal member 25 from be inadvertently separated from the tube portion 23.

A character C formed in a variety of shapes may be fixed on the cap 20.

In this embodiment, when the cap 20 moves upward, the hook portion 26 is hooked on the hook steps 140 formed on the inner portion of the spout hole 11, thereby removing the seal member 25 from the tube portion 23. As a result, the first material stored in the storing space 24 is dropt and mixed with the second material in the container.

The user can drink or use the mixed material through the spout hole 11.

Meanwhile, the seal member 25 is not limited to the above structure. For example, as shown in FIG. 14, a seal member 25 formed in a plate may be attached on a lower end of the tube portion 23 and a hook portion 26 may be formed on a periphery portion of the seal member. The hook portion 26 is hooked on a hook step 140 when the cap 20 moves upward, thereby separating the seal member from the tube portion 23.

In addition, as shown in FIG. 15, a punching portion 143 may be formed on a lower portion of the seal member 25. The punching portion 143 is designed to be hooked on a lower end of the tube portion 23. A packing 144 may be disposed between the seal member 25 and the lower end of the tube portion 23 to enhance the seal force.

FIGS. 16 to 18 show a fifth embodiment of the present invention. In this embodiment, as shown in FIG. 16, the structure includes a spout main body 10 fitted on a container 100, a cap 20 coupled to an upper portion of the main body 10, and an auxiliary cap 30 coupled to the upper portion of the cap 20.

The main body and the cap 20 are similar to those of the fourth embodiment except that the cap 20 is provided with a cap lip portion 150. The cap 20 is further provided at an outer portion with a screw and the auxiliary cap 30 is coupled to the screw to be capable of moving downward by a predetermined distance.

An operating portion 31 is formed on the auxiliary cap 30 to separate the seal member 25 from the tube portion 23 by applying force to the seal member 25. The operating portion is provided with an inclined lower end and a skirt 32 formed on an outer lower portion.

A character C may be fixed on one of the cap and auxiliary cap 20 and 30.

Accordingly, in this embodiment, in a state where the first material is stored in the storing space 24, the skirt is separated with the tube portion 23 on which the seal member 25 is attached. The auxiliary cap moves downward by a distance as long as a distance obtained by separating the skirt.

Then, when the cap 20 is removed from the lip portion 12, the user can drink or use the mixed material through the spout hole. When the cap 20 moves upward, the hook portion 26 of the seal member 25 is hooked on the hook step 140, thereby separating the seal member 25 from the tube portion to allow the mixed material to be more effectively exhausted.

Meanwhile, the coupling of the caps 30 and 20 is not limited to the above. For example, as shown in FIG. 17, a movable member 151 is located in the storing space 24. An inner surface of the movable member 151 is screw-coupled to the operating member 33 formed on the auxiliary cap 30. The movable member 151 is provided at a lower end with an inclined surface 152.

When the auxiliary cap 30 rotates, the movable member 151 screw-coupled to the operating member 33 moves downward. At this point, the seal member 25 is broken by a punch defined by the inclined surface 152, thereby allowing the first material to be dropt and mixed with the second material in the container.

As shown in FIG. 18, an operating member 153 may be screw-coupled to the cap 30, and a peak portion 154 is formed on a lower end of the operating member 153.

Accordingly, when the operating member 153 moves downward, the seal member 25 is broken by the peak portion 154.

FIG. 19 shows a sixth embodiment of the present invention. In this embodiment, a seal member 25 is inserted in a storing space 24 formed in the tube portion 23. The seal member 25 is inserted in a lower end of the tube portion 23 and provided at a periphery with a hook portion 26 hooked on a hook step 140 formed on the spouting hole 11.

A connecting portion 160 vertically extends from the seal member 25 and a wing portion 161 is formed on the connecting portion 160 to effectively release the first material.

The wing portion 161 may be integrally formed with the connecting portion or separated formed and connected to the connecting portion.

In this embodiment, when the cap 20 moved upward by the screw-operation, the hook portion 26 formed on the seal member 25 is hooked on the hook step 140 formed on the spout hole 11, thereby separating the seal member 25 from the tube portion 23.

At this point, when the cap further moves upward, the seal member 25 maintains its fixed state in the spout hole 11. Accordingly, the first material in the storing space 24 is effectively released by the wing portion 26.

Therefore, the first material released from the storing space 24 is effectively mixed with the second material in the container 100. The user can drink or use the mixed material through the spout hole 11.

INDUSTRIAL APPLICABILITY

As described above, the present invention can be applied to any type of containers including a pouch container.

The invention claimed is:

1. A method for mixing different materials in a pouch container comprising the steps of:

storing a first material in a spout assembly fixed on the pouch container;

providing a seal member with a dropping space;

separating a seal member from the spout assembly by moving a cap upwards away from the pouch container, thereby opening the dropping space and releasing the first material into the pouch contain; and mixing the first material with a second material in the container.

2. The method of claim 1, wherein the first material is stored in the cap.

3. The method of claim 1, wherein the first material is stored in a space between the spout assembly and the cap.

4. The method of claim 1, wherein the first material is released into the container by rotating the cap.

5. The method of claim 1, wherein the first material is released into the container by elevating the cap.

6. The method of claim 1, wherein the first material is selected from the group consisting of powder, granule, and liquid.

7. A structure for mixing different materials in a pouch container, comprising:

a spout main body provided with a spout hole through which mixture of a first material and a second material is exhausted;

a cap removably coupled on an outer portion of the spout hole and storing the first material therein;

a seal member coupled to a lower end of a tube portion; and wherein the tube portion is configured to move upward in a direction away from the pouch container and the seal member is provided with a dropping space is opened when the tube portion moves upward.

8. The structure of claim 7, wherein the seal member includes a hook portion hooked on an operating portion formed on a lower portion of the main body, thereby being separated from the tube portion.

9. The structure of claim 8, wherein the hook portion is configured to rotate by a predetermined angle.

10. The structure of claim 7, wherein the spout hole is provided at an inner portion with a circumferential projection.

11. The structure of claim 7, wherein the first material is stored in a space between the spout hole and the tube portion and the seal member is formed of a sheet attached on lower ends of the spout hole and the tube portion.

* * * * *

UNITED STATES PATENT AND TRADEMARK OFFICE

CERTIFICATE OF CORRECTION

PATENT NO. : 7,617,929 B2
APPLICATION NO. : 10/584107
DATED : November 17, 2009
INVENTOR(S) : Lee et al.

It is certified that error appears in the above-identified patent and that said Letters Patent is hereby corrected as shown below:

Col. 7, line 23, change "contain" to --container--.

Col. 8, line 16, change "space is" to --space that is--.

Signed and Sealed this

Ninth Day of February, 2010

David J. Kappos

*Director of the United States Patent and Trademark Office*

UNITED STATES PATENT AND TRADEMARK OFFICE

CERTIFICATE OF CORRECTION

PATENT NO. : 7,617,929 B2
APPLICATION NO. : 10/584107
DATED : November 17, 2009
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 548 days.

Signed and Sealed this

Nineteenth Day of October, 2010

David J. Kappos
*Director of the United States Patent and Trademark Office*